United States Patent [19]
Seddon et al.

[11] Patent Number: 4,499,314
[45] Date of Patent: Feb. 12, 1985

[54] METHANOL CONVERSION TO HYDROCARBONS WITH ZEOLITES AND COCATALYSTS

[75] Inventors: Duncan Seddon; Thomas Mole; Judy A. Whiteside, all of Victoria, Australia

[73] Assignee: Imperial Chemical Industries PLC, London, England

[21] Appl. No.: 605,166

[22] Filed: Apr. 30, 1984

Related U.S. Application Data

[63] Continuation of Ser. No. 367,237, Mar. 31, 1982, abandoned.

[51] Int. Cl.³ ............................................. C07C 1/30
[52] U.S. Cl. ............................... 585/408; 585/357; 585/640; 585/733; 585/639
[58] Field of Search ............... 585/2 SM, 310, 312, 585/315, 357, 733, 640, 408, 409, 469, 639

[56] References Cited

U.S. PATENT DOCUMENTS 3,907,915  9/1975  Chang et al. .
3,998,898 12/1976  Chang et al. .
4,052,479 10/1977  Chang et al. .
4,148,835  4/1979  Chen et al. .
4,156,698  5/1979  Dwyer et al. .
4,232,178 11/1980  Scheper et al. .
4,278,565  7/1981  Chen et al. .

Primary Examiner—Delbert E. Gantz
Assistant Examiner—A. Pal
Attorney, Agent, or Firm—Cushman, Darby & Cushman

[57] ABSTRACT

A process for producing hydrocarbons comprising contacting, under conversion conditions, an aqueous methanol with a crystalline aluminosilicate zeolite catalyst which is hydrothermally stable in the temperature range of from 250° C. to 500° C. and is capable of converting methanol to hydrocarbons, and with a promoter comprising one or more compounds selected from the group consisting of aromatic hydrocarbons, precursors to aromatic hydrocarbons, olefins, precursors to olefins and aldehydes to form a mixture comprising light olefins, lower alkanes and monocyclic aromatic hydrocarbons and recovering said hydrocarbons.

14 Claims, No Drawings

METHANOL CONVERSION TO HYDROCARBONS WITH ZEOLITES AND COCATALYSTS

This is a continuation of application Ser. No. 367,237 filed Mar. 31, 1982, now abandoned.

This invention relates to processes for the production of hydrocarbons from methanol.

The conversion of methanol to hydrocarbons over the zeolite ZSM-5 is well-known as a route to hydrocarbons in the motor-spirit range (Reference: Meisel, S. L., McCullough, J. P., Lechthaller, C. H., and Weisz, P. B., Chem-Tech 6 86 1976). The same zeolite has been reported as a catalyst for the methylation of toluene to para-xylene (Reference: Chem, N. Y., Kaeding, W. W., and Dwyer, F. G., J. Amer. Chem. Soc. 101 6783 1979) and for the production of ethylene and other lower olefins from methanol (Reference: Kaeding, W. W. and Butter, S. A., J. Catalysis 61 155 1980). Particular advantage attaches to the selection and modification of shape-selective zeolites such as the ZSM-5 family of zeolites and to the choice of methanol-containing feedstocks and conditions of catalytic conversion in order that the formation of particularly valuable products such as ethylene and para-xylene may be achieved with maximum speed, selectivity, and reliability.

We have now found that certain compounds fed to a zeolite catalyst along with the methanol-containing feed accelerate the conversion of the methanol to hydrocarbons, particularly olefins and facilitate the control of the reaction. These compounds act as promoters and are referred to hereinafter by this term.

Accordingly we provide a process for the conversion of methanol to hydrocarbons which process comprises passing a methanol-containing feed over a zeolite catalyst wherein there is added to the feed one or more compounds selected from aromatic hydrocarbons and pre-cursors to aromatic hydrocarbons, olefins and pre-cursors to olefins, and aldehydes.

The methanol-containing feed may be methanol itself or mixtures of methanol with other organic or non-organic liquids or vapours. For the selective production of ethylene, a mixture of $C_3$ hydrocarbons rich in propylene, $C_4$ hydrocarbons, and xylenes rich in terms of the para isomer, the feed preferably comprises aqueous methanol having a water:methanol ratio in the range of 1:5 v/v to 5:1 v/v. The rate of delivery of the feed is not narrowly critical and may vary within a range of 0.1–1000 weight hourly space velocity (weight of feed/-weight of catalyst/hour).

The zeolite catalyst may be any zeolite, of natural or synthetic origin, modified or unmodified, which (a) has a channel size such as to permit sorption and diffusion of the promoter, (b) is capable of converting methanol to hydrocarbons in the absence of the promoter, and (c) is hydrothermally stable under suitable conditions at a temperature of at least 250° C. and preferably 500° C.

Without wishing to be limited by any theory as to the selection of a zeolite catalyst for use in accordance with the invention, it is likely that the conversion of methanol to hydrocarbons is dependent upon the Brönsted acidity of the zeolite.

Thus the invention may be applicable to any zeolite which contains Brönsted acidity or is capable of generating Brönsted acidity of sufficient strength to convert methanol to hydrocarbons under the conditions of the reaction. The zeolite would possess a channel structure which would permit the entry of aromatic, olefin, or aldehyde promoter, or a pre-cursor to an aromatic or olefin promoter, to the active site; in the latter case the zeolite would also possess a channel or cage of sufficient dimension to allow the aromatic or olefin promoter to form within the zeolite.

The invention may with particular advantage be applied to the ZSM-5 family of zeolites which possess a channel structure which will permit the entry of certain, less bulky, aromatics and possess Brönsted acidity capable of transforming methanol into hydrocarbons, in a wide variety of forms eg acid (ie de-cationized), zinc exchanged, and magnesium exchanged forms. Where reference is made to ZSM-5 in this specification it is to be understood that those skilled in the art will select one of these forms for carrying out the process of our invention. The proton form, H-ZSM-5, is particularly useful.

In the case of the ZSM-5 zeolite the aluminium content may be varied over the range 0 to 4%. The lower limit of aluminium content of the zeolite approximates in composition to zeolitic silica and may be referred to as silicalite; in this case there will be no Brönsted adidity to convert methanol to hydrocarbons, however it should be noted that ZSM-5 of very low aluminium content, eg silica to alumina molar ratio of 1600:1, does possess sufficient Brönsted acidity to convert methanol to hydrocarbons and therefore could benefit from the promoters of the process of our invention.

The invention is applicable to large port zeolites such as faujasite and mordenites, however for the most beneficial use of the invention these zeolites may have to be transformed by methods known to those skilled in the art to forms which do not possess the normal tendency of these zeolites to produce heavy aromatic products and hence coke. This is best illustrated by the zeolite mordenite, in which the large twelve ring channels permits the build up of large molecules when it is used to convert methanol to hydrocarbons. Thus it is well known that while mordenite will normally give more than 70% of hydrocarbon product heavier than $C_{10}$ from methanol (D H Olson et al J. Phys. Chem. 85 2238 1981), removal of some of the aluminium in the lattice, by methods known to those skilled in the art, substantially reduces the quantity of heavy ($>C_{10}$) material and permits its use to convert methanol to lighter products. The use of modified mordenite in the process of our invention to produce olefins from methanol at moderate temperatures will be described later.

The invention may also be applied to those zeolitic materials of high silica content having multivalent metals other than aluminium contained in the skeletal lattice or the molecular apertures of the zeolites.

The zeolite catalyst may be modified by introducing into the molecular apertures of the zeolite or onto its surface, materials, such as for example compounds of boron, phosphorus, antimony, or silicon, which modify the activity or selectivity of the catalyst.

The aromatic promoters of the process of our invention are aromatic hydrocarbons, for example, benzene and alkylsubstituted benzene hydrocarbons. The aromatic compounds are chosen to be of such size as to adsorb into a diffuse within the zeolite pores. While they should be reactive towards Brönsted acids they should not irreversibly neutralize the acids. The preferred aromatic co-catalysts are benzene, toluene, and para-xylene.

In the particular case of zeolite ZSM-5, para-xylene is a particularly effective promoters while meta-xylene and ortho-xylene are less effective. Since para-xylene is a product of the conversion of methanol over zeolites, it may be recovered from the reaction products and recycled. Where toluene and benzene are used as co-catalysts they will be alkylated under the conditions of conversion to give a mixture of products in which para-xylene predominates. Thus when benzene and toluene are used some of the promotion may be due to the para-xylene formed. Where a major purpose of the conversion is to produce para-xylene from methanol and it is not desired to recycle any of the para-xylene produced, then benzene and toluene may be the preferred promoters.

By pre-cursors of aromatic hydrocarbons we mean compounds which can form aromatic hydrocarbons under the reaction conditions used for the conversion of methanol. These pre-cursors include cycloalkanes and cycloalkenes such as cyclohexane and cyclohexene.

Benzene, toluene and para-xylene are preferred aromatic hydrocarbon promoters for conversion of methanol over ZSM-5 catalyst, but it will be appreciated that other alkylbenzenes, other substituted benzene, and non-benzenoid aromatic compounds can also be effective. It will also be appreciated that the particular choice of aromatic promoters may vary markedly from one zeolite to another.

The preferred olefin promoters are alkenes such as ethylene, propylene and the butenes. It will also be appreciated that zeolite catalysts possessing sufficient Brönsted acidity to convert methanol will be capable of dehydrating alcohols such as ethanol, n-propanol, iso-propanol and higher alcohols to olefins. The use of such olefin pre-cursors may find particular use since they can be miscible in aqueous methanol solutions and this can facilitate the addition of promoters to the system.

Aldehydes, such as formaldehyde, are also effective as promoters under the conditions used for the process of our invention.

The mole ratio of promoters to methanol in the feed may be varied widely within the range of 0.0001:1 to 1:1, preferably in the range of 0.01:1 to 3:1, and most preferably in the range of 0.01:1 to 0.1:1.

The conversion of methanol normally gives a mixture of hydrocarbons. The composition of the mixture depends upon the zeolite catalyst and the temperature and other conditions of conversion. Similarly, the process of the present invention is applicable to the formation of various hydrocarbon mixtures from methanol, but is most advantageously where the hydrocarbon products are reactive, for example as in the cases of ethylene, propylene and the butenes, and where selective formation of particular hydrocarbons is required. In the usual conversion of methanol to hydrocarbons in the gasoline range, a wide range of hydrocarbons is formed which does not include large quantities of ethylene and in which para-xylene is not dominant. Our invention is particularly applicable to the manufacture of hydrocarbon mixtures which contain particularly large amounts of ethylene and para-xylene, generally admixed with large amounts of $C_3$ and $C_4$ hydrocarbons of high olefin-content.

The method of adding the promoter or pre-cursor to the promoter to a process reactor is not narrowly critical and will be readily determined by those skilled in the art. Where the promoter or promoter pre-cursor is miscible with the methanol/water feed in the desired proportions it may be simply incorporated into the feed through suitable conventional mixing means before the methanol/water feed is vapourized for introduction into the reactor. Where methanol and water are fed separately to the reactor, the promoter or promoter pre-cursor may also be fed independently or may be mixed first with one of the other feed components, typically methanol, prior to entry into the reactor. In microreactors used to study process conditions where the methanol/water feed is passed into the reactor by means of an inert carrier gas, typically nitrogen, the same carrier gas may be used to introduce the promoter or promoter pre-cursor.

The process of our invention has several advantages. The process increases the rate of conversion of methanol to hydrocarbons leading to a greater yield in a single pass over the catalyst and thus reducing the need to re-cycle reactants. The rate increases produced by the promoters also allow the conversion to be carried out under lower severity that would give unacceptably low conversion yields with prior art processes. In particular, lower temperatures can be used. Such lower severity conditions facilitate the selective production of lower olefins.

In a further embodiment of our process, the promoter may be used at the beginning or start-up of a conventional conversion process to eliminate the need to use the high starting temperatures common in prior art processes.

In yet a further embodiment of our process, the promoter may be used to improve the activity of a catalyst which for some reason or other has lost part of or has a low innate activity. Thus it can improve the performance of catalysts which have been partly destroyed by over zealous activation or regeneration procedures or improve the activity of a poorly formed catalyst.

The process of our invention is now illustrated by, but not limited to, the following Examples which demonstrate the use of promoters to accelerate the conversion of methanol to hydrocarbon mixtures rich in ethylene and $C_3$ hydrocarbons. The yields are expressed on a weight/weight basis and refer to the total carbon content of the methanol and the other organic components of the feed, which is converted to ethylene, $C_3$ hydrocarbons, p-xylenes and the other desired conversion products. The stated conversions refer to the percentage of the carbon content of the methanol feed converted to hydrocarbons; the remaining carbon is recovered as methanol and dimethyl ether.

For the Examples carried out on the microreactor, product analysis was performed by gas-liquid chromatography (GLC) on two types of columns. The first ('Porapak' Q; 'Porapak' is a registered trade mark) gave good analysis for the light gaseous products, methane, ethylene, ethane, propylene, propane, dimethyl ether, methanol, and $C_4$-hydrocarbons. Analytical results from this column are referred to as "light products".

This analysis is not a true yield in the sense that account was not taken of the differing responses of the flame ionization detector to hydrocarbons on the one hand and oxygenates (methanol, dimethyl ether) on the other. Nevertheless "light products" analysis provides a meaningful measure of the extent of conversion.

The second column (OV101; OV101 is a registered trade mark) provided an analysis of total hydrocarbons from the $C_1$ and $C_2$ to $C_5$ alkyl-aromatics. Analytical results from this column are referred to as "hydrocarbon products" and give an indication of the carbon mass balance.

The fraction of promoter added to the methanol feed of the microreactor via a bubbler may be estimated as follows.

| Promoter | Bubbler temperature | Diluent flow (me/min) | Moles/hour |
|---|---|---|---|
| Benzene | 4° C. | 7 | $6.2 \times 10^{-4}$ |
| Toluene | 0° C. | 7 | $4.2 \times 10^{-5}$ |
| p-Xylene | 20° C. | 7 | $1.5 \times 10^{-4}$ |

The percentage of additive with respect to the feed may be expressed as:

$$\frac{\text{moles (weight) of promoter}}{\text{moles (weight) of methanol}} \times 100$$

For a typical methanol flow (W.H.S.V.; weight hourly space velocity of 1.3 $hr^{-1}$ over 0.2 g catalyst) the percentage of promoter is as shown in the table below.

| | Mole % | Weight % |
|---|---|---|
| Benzene | 1.5 | 9 |
| Toluene | 0.1 | 0.7 |
| p-Xylene | 0.4 | 2.9 |

Product analysis on larger-scale equipment involved the use of four columns including a thermal conductivity detector (TCD) for oxygenates. Here the total product effluent was sampled, and the analysis is given as a volume percentage of the effluent stream.

In the following Examples all parts and percentages are on a weight basis unless otherwise stated.

EXAMPLE 1

This example illustrates the use of aromatic promoters in the conversion of a 1:1 (wt/wt) aqueous methanol solution over the zeolite ZSM-5.

The as-made zeolite ZSM-5 was converted to the active hydrogen form by exchange with 2N hydrochloric acid and calcination to 500° C. in moist air. The product was shown to be H-ZSM-5 by X-ray diffraction of product powder and electron diffraction studies of individual product crystals. The active zeolite contained 1.02% aluminium representing a silica-alumina mole ratio of about 80:1.

To 0.102 g of catalyst (pelleted to 60–80 mesh) was fed a solution of methanol in water (1:1, w/w) at a rate of 1.1 ml $hr^{-1}$ (W.H.S.V. of methanol over the catalyst was about 5.2 $hr^{-1}$). Along with the feed was passed a stream of diluent nitrogen (6 ml $hr^{-1}$) which prior to entry into the reactor could be directed to a bubbler so as to pick up vapours of promoter additive. The products produced were analyzed by GLC and the results are displayed in the Table 1.

The results to process time 4 hrs 50 mins, in the absence of promoter additive, show that a temperature of 295° C. was required to achieve the total conversion of oxygenates (DME), and the yield of ethylene obtained is about 11% by weight of the total hydrocarbons produced at this temperature.

Upon the addition of toluene as an aromatic promoter it is seen that (i) the temperature required to achieve full conversion of the oxygenates is lowered to about 288° C.; and (ii) that the lowering of the temperature required to achieve complete conversion of oxygenates produces an enhanced yield of ethylene (18% by weight of hydrocarbons produced).

TABLE 1

Addition of aromatic promoter in the conversion of a methanol-water mixture over the zeolite ZSM-5

| θ hr. | min | T °C. | Light Products* $C_2H_4$ | $C_3$ | $C_4$ | DME | Hydrocarbon Products** $C_{1,2}$ | $C_3$ | $C_4$ | $C_5+$ | TO | XY | AR |
|---|---|---|---|---|---|---|---|---|---|---|---|---|---|
| 0 | 15 | 319 | | | | | 7 | 12 | 19 | 31 | 5 | 15 | 7 |
| | 40 | 310 | 14 | 28 | 56 | 1 | | | | | | | |
| 1 | 00 | 305 | 16 | 29 | 54 | — | | | | | | | |
| 1 | 20 | 300 | 20 | 28 | 50 | — | | | | | | | |
| 1 | 40 | 291 | 32 | 25 | 42 | — | | | | | | | |
| 2 | 15 | 279 | 11 | 12 | 4 | 74 | | | | | | | |
| 3 | 00 | 290 | 36 | 28 | 17 | 18 | | | | | | | |
| 3 | 15 | 295 | 40 | 28 | 25 | 7 | | | | | | | |
| 3 | 35 | 305 | | | | | 11 | 11 | 15 | 23 | 4 | 17 | 15 |
| 3 | 45 | 305 | 25 | 27 | 45 | — | | | | | | | |
| 4 | 50 | 304 | | | | | 8 | 10 | 17 | 24 | 4 | 16 | 17 |
| 4 | 55 | Nitrogen diluent gas passed through toluene bubbler at °C. | | | | | | | | | | | |
| 5 | 10 | 304 | 17 | 31 | 51 | — | | | | | | | |
| 5 | 35 | 284 | 33 | 30 | 18 | 20 | | | | | | | |
| 6 | 00 | 288 | 33 | 27 | 18 | 2 | | | | | | | |
| 6 | 20 | 288 | | | | | 18 | 17 | 14 | 19 | 5 | 10 | 12 |

Notes:
Θ = Process time
T = Temperature
$C_1, C_2$ etc = Number of carbon atoms
TO = Toluene
XY = Xylenes, ethylbenzene
AR = $C_9$ and higher automatic hydrocarbons
* = Area % (FID)
** = Carbon %
A dash (-) means nil or undetectable

EXAMPLE 2

This example illustrates the benefit of addition of an aromatic promoter in the conversion of a methanol-water feed of higher water content than in the previous example.

The catalyst used was similar in all respects to that described in the previous example. The feed was an aqueous methanol mixture (2.75:1, w/w) which was passed over 0.1 g of the catalyst at 0.66 ml $hr^{-1}$ (the W.H.S.V. of the methanol over the catalyst was about 1.8 hr$^{-1}$). The products were analysed by GLC and are given in Table 2.

The results prior to process time ($\theta$) 6 hr 35 min had no aromatic promoter added and they show that the temperature to achieve complete oxygenate conversion is about 303° C.; this is ca. 10° C. higher than the previous example despite the lowering of the space velocity (W.H.S.V. 1.8 hr$^{-1}$ versus 5.2 hr$^{-1}$) and is presumed due to the higher water content of the feed.

The addition of the toluene promoter has a pronounced effect on the temperature at which complete oxygenate conversion is achieved, namely lowering it to 283° C., 20° C. below that required in the absence of the additive. There is further seen to be a dramatic change in the ethylene yield increasing it from 14% by weight to 22% by weight of the hydrocarbons produced.

The products were analyzed by GLC and are the results displayed in Table 3.

Comparison of these results with those of Examples 1 and 2 show that ethylbenzene improves the conversion of oxygenates to hydrocarbon products in a similar fashion to toluene. It is seen that total conversion of oxygenates can be achieved at about 280° C. raising the ethylene content of the hydrocarbon product to about 24% (wt). After $\theta = 7$ hrs 50 min the hydrocarbon products were sampled and off-line analysis indicated that the xylenes fraction consisted of ethylbenzene, p-xylene, m-xylene and o-xylene in the ratio 2.8:6.2:1.7:1.0. It is thus seen that the p-xylene is formed in greater amounts than expected from the thermodynamic equilibrium which is approximately 1.0:2.0:1.0 for p-xylene:m-xylene:o-xylene. It will thus be appreciated that by the use of an aromatic promoters at low temperatures (<300° C.) xylenes enriched in the para-xylene isomer can be formed using unmodified H-ZSM-5.

TABLE 2

Addition of aromatic promoter in the conversion of a high water-methanol mixture over the zeolite ZSM-5

| $\theta$ | | T | Light Products | | | | Hydrocarbon Products | | | | | |
|---|---|---|---|---|---|---|---|---|---|---|---|---|
| hr. | min | °C. | $C_2H_4$ | $C_3$ | $C_4$ | DME | $C_{1,2}$ | $C_3$ | $C_4$ | $C_{5+}$ | TO | XY | AR |
| 6 | 20 | 303 | 33 | 26 | 39 | 2 | | | | | | | |
| 6 | 35 | 303 | | | | | 14 | 13 | 17 | 21 | 4 | 12 | 16 |
| 6 | 36 | Nitrogen diluent passed through toluene bubbler at 0° C. (6 ml min$^{-1}$) | | | | | | | | | | | |
| 7 | 10 | 320 | 29 | 30 | 40 | — | | | | | | | |
| 7 | 20 | 303 | | | | | 12 | 13 | 15 | 13 | 9 | 17 | 18 |
| 7 | 35 | 292 | 29 | 29 | 41 | — | | | | | | | |
| 7 | 50 | 293 | | | | | 14 | 11 | 14 | 15 | 9 | 16 | 19 |
| 8 | 05 | 283 | 46 | 25 | 28 | — | | | | | | | |
| 8 | 25 | 283 | | | | | 22 | 15 | 13 | 14 | 11 | 14 | 9 |
| 8 | 40 | 280 | 40 | 33 | 18 | 10 | | | | | | | |

EXAMPLE 3

TABLE 3

Addition of ethylbenzene in the conversion of aqueous methanol over the zeolite ZSM-5

| $\theta$ | | T | Light Products | | | | Hydrocarbon Products | | | | | |
|---|---|---|---|---|---|---|---|---|---|---|---|---|
| hr | min | °C. | $C_2H_4$ | $C_3$ | $C_4$ | DME | $C_{1,2}$ | $C_3$ | $C_4$ | $C_{5+}$ | TO | XY | AR |
| 4 | 00 | 274 | 21 | 22 | 2 | 55 | | | | | | | |
| 4 | 01 | Nitrogen diluent diverted through ethyl benzene bubbler at 20° C. (6 ml min$^{-1}$) | | | | | | | | | | | |
| 4 | 20 | 274 | 39 | 25 | 21 | 14 | | | | | | | |
| 4 | 50 | | | | | | 18 | 20 | 17 | 8 | 1 | 25* | 11 |
| 5 | 25 | 269 | 30 | 28 | 11 | 29 | | | | | | | |
| 5 | 26 | Ethylbenzene addition stopped | | | | | | | | | | | |
| 6 | 00 | 269 | 19 | 21 | 6 | 53 | | | | | | | |
| 6 | 30 | Ethylbenzene addition restarted | | | | | | | | | | | |
| 7 | 00 | 270 | 29 | 28 | 12 | 31 | | | | | | | |
| 7 | 30 | 280 | | | | | 24 | 21 | 13 | 12 | 2 | 16* | 9 |
| 7 | 50 | 290 | | | | | 17 | 12 | 13 | 11 | 3 | 21* | 18 |

*contains ethylbenzene

This example illustrates the use of a different aromatic promoter, ethylbenzene, in improving the reactivity of the zeolite ZSM-5 in converting a methanol/water mixture to hydrocarbons and improving the selectivity of the products produced to those of highest value, namely, ethylene and para-xylene.

The catalyst used was that described for Example 1. It had been regenerated prior to use by burning off carbonaceous residues in all atmosphere of oxygen at 500° C. The feed was a 2.75:1 (w/w) aqueous methanol which was passed over 0.1 g of the catalyst at a rate of 1.1 ml hr$^{-1}$ (the W.H.S.V. of the methanol over the catalyst was about 2.8 hr$^{-1}$). The bubbler providing the aromatic promoter contained ethylbenzene at 20° C.

EXAMPLE 4

This example illustrates the use of toluene as an aromatic promoter in improving the reactivity of ZSM-5 in converting aqueous dimethylether to hydrocarbon products rich in ethylene.

The ZSM-5 catalyst used was that described for Example 1 and it had been regenerated prior to use by burning off the carbonaceous deposits in an atmosphere of oxygen at 500° C. for 1 hr. The feed consisted of water, which was delivered at the rate of 1.1 ml hr$^{-1}$ and dimethyl ether which was delivered at the rate of about 6 ml min$^{-1}$. Nitrogen diluent was also passed over the catalyst at about the same rate; this diluent could be diverted through a bubbler containing toluene to deliver toluene vapour to the reaction system. The products produced were analyzed by GLC and the results are displayed in Table 4.

From the results it is readily seen that the addition of toluene promoters allows the temperature at which total dimethylether conversion is achieved to be reduced by almost 20° C. (274° cf 292°). It will also be appreciated that high conversion to ethylene is achieved (21% (wt) of hydrocarbon products).

TABLE 4

Conversion of dimethylether in the presence of water over ZSM-5 with an aromatic promoter

| Sample No | T °C. | % Conversion | Hydrocarbon Products |  |  |  |  |  |  |
|---|---|---|---|---|---|---|---|---|---|
|  |  |  | $C_{1,2}$ | $C_3$ | $C_4$ | $C_{5+}$ | T | X | $C_{9A+}$ |
| 1 | 302 | 100 | 15 | 12 | 14 | 20 | 3 | 15 | 16 |
| 2 | 292 | 100 | 23 | 17 | 14 | 18 | 3 | 14 | 9 |
| 3 | 282 | 80 | 18 | 18 | —* | 14 | 2 | 9 | 12 |
| Nitrogen diverted through toluene bubbler at 0° C. |  |  |  |  |  |  |  |  |  |
| 4 | 274 | 100 | 21 | 21 | 13 | 12 | 9 | 14 | 5 |

*DME was present in the $C_4$ analysis

EXAMPLE 5

This example illustrates the use of an aromatic promoter in improving the reactivity of the zeolite ZSM-11 towards the conversion of methanol/water to hydrocarbons, in particular to light olefins.

The zeolite ZSM-11 was synthesised in a manner similar to that described in U.S. Pat. No. 4,108,881 using 1,8-octanediamine as organic cation source. The as-made material was transformed to the active, hydrogen form by exchange with 2N hydrochloric acid and calcination to 500° C. in a moist air atmosphere. The product was shown to be ZSM-11 by X-ray diffraction of the powder product and electron diffraction of some individual crystals of product. The acid form contained 0.96% and representing a silica to alumina mole ratio of about 85:1.

To 0.201 g of catalyst (pelleted to 60–80 mesh) was fed a solution of methanol in water (1:1, wt/wt) at a rate of 1.1 ml hr$^{-1}$ (the W.H.S.V. of methanol over the catalyst was about 2.6 hr$^{-1}$). Along with the feed was passed a stream of diluent nitrogen (6 ml min$^{-1}$) which prior to entry into the reactor could be diverted to a bubbler so as to pick up vapours of aromatic additive. The products produced were analyzed by GLC and the results are displayed in Table 5.

The results to process time ($\theta$) 4 hr 53 min, in the absence of additive, show that (i) a temperature of at least 320° C. was required for the steady and total conversion of oxygenates (DME). (ii) The ZSM-11 catalyst shows hysteresis in that when the temperature is lowered to 300° C. there is a substantial loss in activity (as witnessed by the poor conversion of oxygenates), which is not restored by an increase in temperature to 320° C.

After 5 hrs on stream toluene addition was commenced. The results to $\theta = 5$ hr 53 min show that (i) $C_9$ and higher aromatics are not significantly higher than are observed in the hydrocarbon product formed in the absence of toluene ie the increased conversion is not due solely to methylation reactions and (ii) the addition of toluene permits the reaction temperature to be lowered below 320° C. and still maintain total oxygenate conversion.

At $\theta = 6$ hr the addition of toluene was stopped and the result at $\theta = 6$ hr 33 min illustrates that total conversion is maintained; for 30 minutes, ie the reaction has been "switched-on" by the addition of the aromatic. A further lowering of the temperature ($\theta = 7$ hr 23 min; 301° C.) results in loss in activity which is restored by recommencement of the addition of toluene ($\theta = 7$ hr 50 min; 302° C.). It is thus seen that addition of aromatic co-catalyst can lower the temperature at which total conversion of oxygenates can be achieved by 20° C. over the catalyst ZSM-11.

Since the olefin component of the hydrocarbon product is increased by the lowering of reaction temperatures (and hence improved thermal stability) it can be seen that this invention is particularly suited to light olefin synthesis; compare, for example, the yields of ethylene obtained at total oxygenate conversion in the absence of aromatic additive (7% by weight; $\theta = 0$ hr 4 min; T = 320° C.) and with aromatic additive (13% by weight; $\theta = 6$ hr 33 min; T = 310° C.).

TABLE 5

Addition of aromatic promoter in the conversion of methanol-water over the zeolite ZSM-11

| $\theta$ |  | T | Light Products |  |  |  | Hydrocarbon Products |  |  |  |  |  |
|---|---|---|---|---|---|---|---|---|---|---|---|---|
| hr | min | °C. | $C_2H_4$ | $C_3$ | $C_4$ | DME | $C_{1,2}$ | $C_3$ | $C_4$ | $C_{5+}$ | TO | XY | AR |
| 0 | 04 | 320 |  |  |  |  | 7 | 12 | 21 | 27 | 3 | 10 | 19 |
| 0 | 28 | 301 | 28 | 27 | 43 | 0.9 |  |  |  |  |  |  |  |
| 1 | 03 | 295 | 3 | 4 | 2 | 90 |  |  |  |  |  |  |  |
| 1 | 23 | 303 | 7 | 8 | 4 | 81 |  |  |  |  |  |  |  |
| 1 | 38 | 310 | 12 | 13 | 12 | 63 |  |  |  |  |  |  |  |
| 2 | 07 | 318 | 22 | 25 | 43 | 9 |  |  |  |  |  |  |  |
| 2 | 33 | 320 | 20 | 27 | 46 | 6 |  |  |  |  |  |  |  |
| 2 | 48 | 330 |  |  |  |  | 6 | 11 | 20 | 25 | 3 | 11 | 25 |
| 3 | 07 | 330 | 15 | 29 | 53 |  |  |  |  |  |  |  |  |
| 3 | 23 | 329 |  |  |  |  | 4 | 10 | 17 | 25 | 4 | 12 | 28 |
| 4 | 43 | 329 | 17 | 29 | 53 |  |  |  |  |  |  |  |  |
| 4 | 53 |  |  |  |  |  | 8 | 12 | 21 | 27 | 3 | 12 | 12 |
| 5 | 00 | $N_2$ diluent gas passed through toluene bubbler at 0° C. |  |  |  |  |  |  |  |  |  |  |  |
| 5 | 18 | 329 |  |  |  |  | 5 | 10 | 16 | 22 | 4 | 15 | 28 |
| 5 | 38 | 329 | 17 | 32 | 50 | — |  |  |  |  |  |  |  |
| 5 | 53 | 309 | 23 | 28 | 48 | — |  |  |  |  |  |  |  |
| 6 | 00 | toluene addition stopped |  |  |  |  |  |  |  |  |  |  |  |
| 6 | 33 | 310 |  |  |  |  | 13 | 12 | 15 | 22 | 3 | 9 | 24 |
| 7 | 23 | 301 | 12 | 11 | 16 | 61 |  |  |  |  |  |  |  |
| 7 | 30 | toluene addition recommenced |  |  |  |  |  |  |  |  |  |  |  |
| 7 | 40 | 302 |  |  |  |  | 11 | 9 | 13 | 29 | 3 | 12 | 27 |

TABLE 5-continued

Addition of aromatic promoter in the conversion of methanol-water over the zeolite ZSM-11

| θ | | T | Light Products | | | | Hydrocarbon Products | | | | | |
|---|---|---|---|---|---|---|---|---|---|---|---|---|
| hr | min | °C. | $C_2H_4$ | $C_3$ | $C_4$ | DME | $C_{1,2}$ | $C_3$ | $C_4$ | $C_{5+}$ | TO | XY | AR |
| 7 | 50 | 302 | 24 | 19 | 50 | 4 | | | | | | | |
| 7 | 51 | toluene addition stopped | | | | | | | | | | | |
| 8 | 00 | | 13 | 12 | 7 | 68 | | | | | | | |

EXAMPLE 6

This example illustrates the use of an aromatic promoter in the conversion of a water-methanol mixture (1:1, w/w) over another catalyst of the ZSM-5 family.

A zeolite of the ZSM-5 family was prepared in a similar manner to that described in U.S. Pat. No. 3,709,979 using tetrabutylammonium as the source of the organic cation. The as-made material was transformed to the active hydrogen form by exchange with 2N hydrochloric acid and calcination to 500° C. in moist air. The product was shown to be of the ZSM-5/ZSM-11 family but being neither of these two materials by X-ray diffraction of product powder and electron diffraction studies of some individual crystals of product. The active zeolite contained 0.85% Al representing a silica to alumina mole ratio of about 100:1.

To 0.20 g of catalyst (pelleted to 60–80 mesh) was fed a solution of methanol and water (1:1, wt/wt) at a rate of 1.1 ml hr$^{-1}$ (W.H.S.V. of methanol over the catalyst was about 206 hr$^{-1}$). Along with the feed was passed a stream of diluent nitrogen (6 ml min$^{-1}$) which prior to entry into the reactor could be diverted so as to pick up vapours of aromatic additives. The products produced were analyzed by GLC and the results displayed in Table 6.

The results to process time (θ) 3 hr 20 min in the absence of aromatic additive show that a temperature of at least 300° C. is required to obtain total conversion of the oxygenates and at about this temperature (311° C.) the amount of ethylene obtained is 11% (C%) of the hydrocarbon products.

After 3 hrs 25 min on-stream-time toluene was added to the system and the results to 6 hrs 35 min demonstrates that (i) the temperature at which total conversion of oxygenates is obtained is considerably lower, ~286° vs 303°, and that (ii) the ethylene yield is improved (16% (C%) of hydrocarbons).

TABLE 6

Addition of aromatic promoter in the conversion of methanol (with water) over a zeolite of the ZSM-5/ZSM-11 family

| θ | | T | Light Products | | | | Hydrocarbon Products | | | | | | |
|---|---|---|---|---|---|---|---|---|---|---|---|---|---|
| hr | min | °C. | $C_2H_4$ | $C_3$ | $C_4$ | DME | $C_{1,2}$ | $C_3$ | $C_4$ | $C_{5+}$ | TO | XY | AR |
| 0 | 30 | 312 | 23 | 28 | 48 | — | | | | | | | |
| | 50 | 300 | 34 | 25 | 40 | — | | | | | | | |
| 1 | 10 | 289 | 29 | 25 | 16 | 30 | | | | | | | |
| 1 | 35 | 298 | 35 | 25 | 28 | 8 | | | | | | | |
| 1 | 55 | 303 | 31 | 23 | 42 | 3 | | | | | | | |
| 2 | 25 | 311 | | | | | 11 | 11 | 18 | 24 | 3 | 13 | 15 |
| 2 | 45 | 311 | 23 | 25 | 49 | — | | | | | | | |
| 3 | 20 | 311 | | | | | 9 | 11 | 17 | 25 | 4 | 14 | 17 |
| 3 | 25 | Nitrogen diluent passed through toluene bubbler | | | | | | | | | | | |
| 3 | 45 | 311 | | | | | 7 | 10 | 16 | 21 | 4 | 17 | 20 |
| 4 | 10 | 311 | 20 | 31 | 47 | — | | | | | | | |
| 4 | 25 | 292 | 30 | 27 | 42 | — | | | | | | | |
| 4 | 55 | 292 | | | | | 13 | 10 | 13 | 22 | 4 | 15 | 17 |
| 5 | 30 | 291 | 38 | 24 | 36 | — | | | | | | | |
| 5 | 45 | 286 | 40 | 28 | 25 | 7 | | | | | | | |
| 6 | 15 | 286 | | | | | 16 | 13 | 12 | 16 | 4 | 13 | 18 |
| 6 | 35 | 286 | 36 | 26 | 22 | 13 | | | | | | | |
| 6 | 36 | Toluene addition stopped | | | | | | | | | | | |
| 67 | 00 | 286 | 22 | 21 | 9 | 46 | | | | | | | |

EXAMPLES 7–19

A microreactor was charged with ZSM-5 (0.2 g), prepared as described in Example 1, and used to study the influence of various additives upon the conversion of a water/methanol mixture (2.75:1, w/w). The catalyst had been used many times prior to these examples and so its activity was inferior to that described in the previous examples. The various additives to be tested were added to the feed by means of a small bubbler containing about 2 ml of additive under test. Nitrogen was passed through this bubbler at 7 ml min$^{-1}$ and the resulting mixture of nitrogen and additive vapours fed to the reactor along with the methanol/water feed. The temperature of the reactor was maintained at 310°. Parallel experiments with the same feed, catalyst, and reaction conditions were carried out in each case without additive in the bubbler. The results of these parallel experiments are given for comparison.

EXAMPLES 7–10

These show the effect of the preferred aromatic hydrocarbons which are of a size that does not interfere with access to active sites in the zeolite ZSM-5.

TABLE 7

| | | | % Light Products | | |
|---|---|---|---|---|---|
| Example | Additive | Temperature of bubbler | $C_2H_4$ | $C_3H_6$ and $C_3H_8$ | DME |
| 7 | Benzene | Ambient | 39 | 33 | 7 |
| | (Nitrogen) | Ambient | 28 | 24 | 38 |
| 8 | Toluene | 0° C. | 35 | 28 | 12 |
| | (Nitrogen) | 0° C. | 25 | 22 | 34 |

TABLE 7-continued

| Example | Additive | Temperature of bubbler | % Light Products | | |
|---|---|---|---|---|---|
| | | | $C_2H_4$ | $C_3H_6$ and $C_3H_8$ | DME |
| 9 | Para-xylene | Ambient | 29 | 23 | 29 |
| | (Nitrogen) | " | 27 | 24 | 32 |
| 10 | n-Propyl-benzene | Ambient | 31 | 25 | 22 |
| | (Nitrogen) | " | 14 | 27 | 68 |

EXAMPLES 11–13

These examples illustrate the use of ortho- and meta-substituted, and bulky alkyl-substituted aromatics which are less preferred promoters for the zeolite ZSM-5.

TABLE 8

| Example | Additive | Temperature of bubbler | Light Products | | |
|---|---|---|---|---|---|
| | | | $C_2H_4$ | $C_3H_6$ and $C_3H_8$ | MeOH DME* |
| 11 | Ortho-xylene | Ambient | 22 | 20 | 41 |
| 12 | Meta-xylene | Ambient | 35 | 24 | 10 |
| | Nitrogen | " | 13 | 13 | 68 |
| 13 | Cumene | Ambient | 20 | 19 | 52 |
| | Nitrogen | | 21 | 19 | 54 |

EXAMPLES 14–19

These illustrate the use of cycloalkanes, cycloalkenes, olefins, alcohols and aldehydes, as promoters.

TABLE 9

| Example | Additive | Temperature of bubbler | % Light products | | |
|---|---|---|---|---|---|
| | | | $C_2H_4$ | $C_3H_6$ and $C_3H_8$ | MeOH DME* |
| 14 | Cyclo-hexane | Ambient | 29 | 26 | 31 |
| | Nitrogen | " | 20 | 19 | 52 |
| 15 | Cyclo-hexane | Ambient | 28 | 29 | 4 |
| | Nitrogen | " | 32 | 27 | 18 |
| 16 | Pentene | −78° C. | 30 | 26 | 25 |
| | Nitrogen | " | 19 | 17 | 56 |
| 17 | Ethylene (with feed) | Ambient | — | 15 | 5 |
| | Nitrogen | " | 23 | 20 | 46 |
| 18 | Ethanol | 0° C. | 35 | 21 | 28 |
| | Nitrogen | " | 24 | 21 | 41 |
| 19 | Formaldehyde | 0° C. | 28 | 22 | 35 |
| | Nitrogen | " | 16 | 15 | 63 |

EXAMPLES 20–28

These examples further illustrate the use of the invention in improving the yields of ethylene and paraxylene from methanol over the zeolite ZSM-5. In previous examples the zeolite was in well formed crystals (rice grain in shape size 0.9μ thick by 2.4μ long).

In the following examples the ZSM-5 was the result of a seeded route (see for example U.S. Pat. No. 4,275,947) and consisted of distorted oval, hexagonal and rectangular pieces. The poor crystalline form of this material was probably responsible for its low innate activity with respect to the ZSM-5 used in Example 1.

EXAMPLE 20

This is a comparative example of the typical prior art process which does not contain a promoter according to the present invention.

ZSM-5 catalyst (0.15 g of 60–80 mesh and containing 1.14% aluminium and 0.03% sodium) was packed into a quartz reactor tube of 6 mm outside diameter. The reactor tube was held at 289° C. and was fed with 1.1 ml/hour of a water/methanol mixture (2:1 v/v) and 7 ml/minute of nitrogen gas. Conversion to hydrocarbons was less than 10% and the yield of total $C_{2-3}$ hydrocarbons was less than 5%.

EXAMPLE 21

The experiment of Example 20 was repeated but with the 7 ml/minute stream of nitrogen gas bubbled through toluene at 0° C. About 50% of the methanol was converted to hydrocarbons and the yields were: ethylene 10%, $C_3$ hydrocarbons 12%, toluene 14% and xylenes 9%. The xylenes were 70% para-isomer, 14% meta and 16% ortho.

EXAMPLE 22

The experiment of Example 21 was repeated but at a reactor temperature of (309° C.). The conversion to hydrocarbons was 80% and yields were: ethylene 17%, $C_3$ hydrocarbons 18%, toluene 11% and xylenes 19%.

EXAMPLE 23

ZSM-5 zeolite (0.15 g) was placed in a reactor tube at 319° C. and fed with water/methanol (2:1 v/v) at a rate of 1.1 ml hr$^{-1}$ and nitrogen gas at a rate of 2 ml min$^{-1}$ bubbled through toluene at 0° C. Conversion to hydrocarbons was complete, and the yields were: ethylene 20%, $C_3$ hydrocarbons 20%, $C_4$-$C_7$ non-aromatic hydrocarbons 20%, toluene 10%, xylene 19%, and aromatic hydrocarbons of >8 carbon atoms 7%. The xylenes consisted of 80% para isomer, 12% meta and 8% ortho.

EXAMPLE 24

The experiment of Example 23 was repeated except in that the 2 ml/minute of nitrogen was bubbled through benzene at 0° C. instead of toluene. The conversion of methanol to hydrocarbons was 80% and the yields were: ethylene 16%, $C_3$ hydrocarbons 17%, $C_{4-7}$ non-aromatic hydrocarbons 9%, benzene 10%, toluene 6%, xylenes 14% and aromatic hydrocarbons of >8 carbon atoms 4%.

EXAMPLE 25

This is a comparative example of a prior art process.

ZSM-5 zeolite (0.15 g) of Example 20 was placed in a reactor tube at 289° C. and fed with 1.1 ml/minute of water/methanol (2:1 v/v) and nitrogen gas at a rate of 7 ml/minute. Conversion of methanol to hydrocarbons was 15%. The yields were: ethylene 3½%, $C_3$ hydrocarbons 5% and xylenes 2%.

EXAMPLE 26

The experiment of Example 25 was repeated except that the nitrogen stream was bubbled through paraxylene at 20° C. The conversion of methanol to hydrocarbons was 95%, and the yields were: ethylene 9%, $C_3$ hydrocarbons 12%, and xylenes 20%.

EXAMPLE 27

This is another comparative example of a prior art process.

ZSM-5 (0.15 g) was placed in tube at 310° C. and fed with dry methanol at a rate of 1.1 ml/hour and nitrogen gas at a rate of 4.5 ml/minute. Conversion of methanol to hydrocarbons was 45%, and the yields were: ethylene 13%, $C_3$ hydrocarbons 14%, and xylenes 5%.

EXAMPLE 28

The experiment of Example 27 was repeated except that the nitrogen was bubbled through para-xylene at 20° C. Conversion of methanol to hydrocarbons was 60% and the yields were: ethylene 15%, $C_3$ hydrocarbons 16%, and xylenes 7%.

EXAMPLES 29–31

The following examples illustrate the use of the invention in converting methanol to hydrocarbons, particularly ethylene and para-xylene, on a larger scale than previously described.

The zeolite used was ZSM-5 which was synthesized in a similar manner to that described in Example 1. The zeolite (10 g) was fabricated into ⅛ inch extrudates using alumina as binder (30% w/w). The extruded product was charged into a vertical down flow reactor which could be maintained under isothermal conditions by means of an external electrical furnace. Above the catalyst bed (9 cm long) was placed inert alumina (about 11 cm) and then a bed of active alumina (10 cm). The aim of this bed packing was to remove some of the heat of reaction in the zeolite bed by converting methanol into dimethyl ether before the reactants came into contact with the zeolite. Aqueous methanol (2.75:1; w/w) was used as reactant feed and was delivered as a vapour to the reactor via a reservoir, metering pump and vapourisor. The space velocity (W.H.S.V.) of methanol over the catalyst was 1.33 $hr^{-1}$. The reaction temperature could be assessed by means of three thermocouples placed in the reactor bed. The gaseous effluent from the reaction was analyzed, without cooling to remove water, by an on-line GLC system. No additional diluent (eg nitrogen) was co-fed with the feed or promoter. The latter was added to the system by a separate metering pump which fed the promoter directly into the vapouriser.

EXAMPLE 29

This example shows the effect of the addition of 5% of toluene (w/w based on methanol feed) in improving the conversion and ethylene yield from an aqueous methanol feed (2.75:1, w/w). The results are displayed in Table 10.

TABLE 10

| θ | | | Products (Vol % of Effluent)** | | | | | | | | |
|---|---|---|---|---|---|---|---|---|---|---|---|
| hr | min | Tmax* | $H_2O$ | DME | MeOH | $C_2H_4$ | $C_3H_6$ | $C_3H_8$ | $C_4$ | TO | XY |
| 0 | 30 | 284 | 86.6 | 5.51 | 5.19 | — | — | — | — | — | — |
| 0 | 43 | toluene additional started | | | | | | | | | |
| 2 | 11 | 349 | 94.8 | — | — | 1.10 | .37 | .46 | .83 | .11 | .29 |
| 2 | 19 | toluene additional stopped | | | | | | | | | |
| 3 | 09 | 338 | 93.7 | — | — | 1.85 | .54 | .36 | .83 | .04 | .23 |
| 5 | 50 | 298 | 87.2 | 4.01 | 4.80 | 0.50 | .37 | .02 | — | — | .01 |
| 6 | 40 | 297 | 86.7 | 4.45 | 4.98 | 0.37 | .28 | .01 | — | — | .01 |

*Tmax is maximum bed temperature
**residual inerts to 100%

These results illustrate that by addition of the promoter the reaction can be moved from a position of no conversion of oxygenates to hydrocarbons to a position of 100% oxygenate conversion. The yield of ethylene is the greatest of the hydrocarbon products, not xylenes which might be expected if the reaction is due solely to toluene alkylation. After the toluene addition is stopped the beneficial effects of promoter addition is slowly lost as witnessed by the fall in reaction temperature, and oxygenate breakthrough.

EXAMPLE 30

This example shows the beneficial effect of 1% (w/w) toluene addition. The catalyst and conditions were as Example 29, the catalyst being used without regeneration. The results are displayed in Table 11.

TABLE 11

| θ | | | Products (Vol % of Effluent) | | | | | | | | |
|---|---|---|---|---|---|---|---|---|---|---|---|
| hr | min | Tmax | $H_2O$ | DME | MeOH | $C_2H_4$ | $C_3H_6$ | $C_3H_8$ | $C_4$ | TO | XY |
| 1 | 00 | 295 | 87.2 | 5.00 | 5.02 | 0.23 | 0.15 | 0.01 | 0.92 | — | — |
| 1 | 40 | | 10 % toluene added | | | | | | | | |
| 2 | 10 | 320 | 94.0 | — | — | 2.00 | 0.59 | 0.33 | 0.74 | 0.03 | 0.17 |
| 2 | 20 | | Toluene addition stopped | | | | | | | | |
| 3 | 20 | 330 | 93.9 | — | — | 1.84 | 0.52 | 0.33 | 0.80 | .04 | .16 |

This example shows that aromatic addition at very low levels of methanol fed (eg 1% w/w) is effective in increasing the conversion and improving the yields of light olefins. The example also shows the effect is persistent in that once started by addition of promoter, the reaction can continue without continuous additive addition. It will be appreciated that for extended periods of running it may be beneficial (eg economical) to add co-catalyst intermittently during a run.

EXAMPLE 31

This example illustrates the intermittent feeding of additive (toluene at 5% w/w of methanol feed). The catalyst and conditions were as those in Example 29; the catalyst was used without regeneration. The results are displayed in Table 12.

TABLE 12

| θ hr | min | Tmax | Products (Vol % of Effluent) | | | | | | | | |
|---|---|---|---|---|---|---|---|---|---|---|---|
| | | | $H_2O$ | DME | MeOH | $C_2H_4$ | $C_3H_6$ | $C_3H_8$ | $C_4$ | TO | XY |
| 0 | 49 | 304 | 86.4 | 3.78 | 4.63 | 0.67 | 0.37 | 0.34 | 0.06 | — | .01 |
| 0 | 52 | | 5% toluene added | | | | | | | | |
| 1 | 48 | 350 | 93.5 | — | — | 1.26 | 0.41 | 0.47 | 0.90 | 0.15 | 0.29 |
| 2 | 07 | 359 | toluene addition stopped | | | | | | | | |
| 3 | 00 | 334 | 92.6 | — | — | 1.99 | 0.59 | 0.27 | 0.75 | 0.03 | 0.14 |
| 4 | 20 | 334 | 90.9 | — | — | 2.35 | 0.88 | 0.20 | 0.61 | 0.02 | 0.13 |
| 5 | 25 | 306 | 87.2 | 2.83 | 4.01 | 0.92 | 0.59 | 0.03 | 0.09 | 0.003 | 0.02 |
| 6 | 05 | | 5% toluene added for 5 minutes only | | | | | | | | |
| 6 | 40 | 356 | 92.5 | — | — | 1.40 | 0.45 | 0.43 | 0.80 | 0.11 | 0.26 |

This example shows that as the conversion of oxygenates brought about by the use of aromatic promoter falls away and the light olefin yield falls also, both can be restored by the additive of small quantities of aromatic promoters. In this instance the improved performance after $\theta = 6$ hr 5 min is brought about by the addition of only 0.06 g of promoter to the process feed (feed rate 50 cc per hour).

EXAMPLE 32

This example demonstrates the use of the invention in converting methanol to useful hydrocarbon products using a faujasite zeolite.

Sodium Y (4 g) was mixed to a thick paste with 2N acetic acid. This was then dried at 200° C. for 3 hrs, broken then sieved to 20–200 mesh. The sample was then packed into a quartz tube and fired at 400° C. overnight, in a tubular furnace, under an atmosphere of nitrogen. The nitrogen flow (10 ml min$^{-1}$) was then passed through silicon tetrachloride (12.8 g) in a bubbler and the catalyst heated over the range 360° to 520° C. During this period the quartz tube was occasionally rotated to ensure a uniform treatment. After this dealuminization step the product was washed with boiling water (3×200 ml) filtered and washed with copious quantities of distilled water. The product was then dried at 110° C. for 3 hours. The crude washed, dealuminized Na-Y was then acid washed with 0.3M hydrochloric acid. The aluminium content of the product was 1.04%.

The resulting product (0.2 g) was packed into a microreactor and tested in a similar manner to that described in Example 1. In this example, however, neat methanol was used as feed, which was passed over the catalyst at a space velocity (W.H.S.V.) of about 1.4 hr$^{-1}$. The products were analysed by GLC and the results are displayed in Table 13.

TABLE 13

The conversion of methanol over dealuminated zeolite Y aided by aromatic promoter

| Sample | Temperature | Promoter | $C_2H_4$ % Yield |
|---|---|---|---|
| 1 | 373° C. | nil | 2% |
| 2 | 373° C. | p-xylene | 7% |
| 3 | 373° C. | p-xylene | 6% |
| 4 | 373° C. | nil | 2% |

*$CH_4$, $C_2H_6$ are less than 5% of $C_2H_4$.
Conversion in all cases was below 100%

From the table it is seen that the use of p-xylene as promoter improves the yield of ethylene, hence demonstrating the potential use of dealuminized large port faujasites for the production of ethylene from methanol brought about by the process of the invention.

EXAMPLES 33–36

The following Examples show the use of the invention in improving the ability of mordenite to convert methanol to useful hydrocarbons. The prior art teaches that 70% of the products from the conversion of methanol to hydrocarbons are molecules with a carbon number greater than ten. These products will act as coke precursors and explains the short lifetimes observed for mordenite catalysts. Those skilled in the art know that the very high fouling rate can be overcome by addition of a metal, especially a transition metal, and the use of high hydrogen partial pressure. Such an hydrogen reducing system tends to give alkanes rather than alkenes which mitigates against its use as a method of preparing alkenes. Those skilled in the art also know that the fouling of mordenite catalysts can be partially overcome by reducing the aluminium content of the mordenite. Obviously this has to be done in a manner such that the number of Brönsted sites available for catalysis still gives a useful rate of conversion, and that the dealumination does not cause the destruction of mordenite structure. The amount of dealuminzation for a viable catalyst system is easily determined by those skilled in the art. The following examples are illustrative of the use of dealuminized mordenite in preparing useful hydrocarbons from methanol and how improvements can be made using our invention of promoter addition.

EXAMPLE 33

This is a comparative example illustrating the use of a prior art method to improve the performance of mordenite in conversion of methanol to useful hydrocarbon products.

Hydrogen mordenite ('Zeolon' 100H; 'Zeolon' is a registered trade mark) was dealuminized by refluxing the powder in hydrochloric acid (6N) for 6 hours. The product was filtered off, washed with deionized water, dried and then compacted to 60–100 mesh size. The product contained 0.85% aluminium.

The catalyst (0.2 g) was charged into a microreactor and tested in a similar manner to that described in Example 1. The feed used was methanol which was passed over the catalyst at a space velocity (W.H.S.V.) of 2.4 hu$^{-1}$ along with nitrogen as carrier at 7 ml min$^{-1}$. The products were analyzed by GLC and the results displayed in Table 14.

The results demonstrate that dealuminized mordenite at moderate temperature is capable of converting methanol to a hydrocarbon product which contains significant quantities of light olefins. The production of heavy aromatics was low (14.1% of products of $C_{9+}$ aromatics compared to untreated mordenites >70% ($C_{10+}$ aromatics) as was the production of methane and ethane (both high in untreated mordenite). It is however seen that although the fouling rate is improved the catalyst has extensively decayed after 41 mins on-stream-time.

TABLE 14

The Conversion of Methanol over Dealuminized Mordenite (A) % Light Products

| θ Min | Temp °C. | $CH_4$ | $C_2H_4$ | $C_2H_6$ | $C_3H_6$ | $C_3H_8$ | $C_4$ | DME |
|---|---|---|---|---|---|---|---|---|
| 10 | 329 | 3.5 | 14.0 | 0.7 | 32.6 |  | 49.1 | — |
| 21 | 331 |  |  |  |  |  |  |  |
| 41 | 330 | 2.3 | 11.1 | 0.5 | 12.2 | 5.9 | 8.3 | >59 |

(B) % Hydrocarbons

| θ Min | Temp °C. | $C_{1,2}$ | $C_3$ | $C_4$ | TO | XY | AR |
|---|---|---|---|---|---|---|---|
| 10 | 329 |  |  |  |  |  |  |
| 21 | 331 | 18 | 25.7 | 27.8 | 3 | 0 | 14.1 |
| 41 | 330 |  |  |  |  |  |  |

EXAMPLE 34

Hydrogen Mordenite ('Zeolon' 100H) was dealuminized by refluxing the powder with nitric acid (6N) for 4 hours. The product was filtered off washed with deionised water, dried, then compacted to 60–100 mesh size. The product contained 0.95% aluminium.

The catalyst (0.2 g) was charged into a microreactor and tested in a similar manner with similar results to that described in Example 33. The catalyst was used several times and was regenerated in oxygen at 520° C., cooled and was then used to convert an aqueous methanol feed (2.75:1; w/w). The feed was passed over the zeolite at a rate such that the space velocity (W.H.S.V.) of the methanol was 1.30 hr$^{-1}$. A stream of diluent nitrogen (7 ml min$^{-1}$) was also passed over the zeolite to carry away hydrocarbon products, which were then analyzed by GLC and are reported in Table 15.

The results show that under the test conditions at 284° C. the dealuminized mordenite does not convert methanol in aqueous solution to hydrocarbon products; however upon addition of p-xylene almost complete conversion is achieved with substantial quantities of products being formed as light olefins. It should be noted that at this low temperature of conversion which is only achieved by means of the invention the formation of $C_{9+}$ aromatics is low.

TABLE 15

The influence of p-xylene as aromatic promoter on the conversion of Aqueous methanol feed over dealuminized mordenite (A) % Light Products

| θ Min | Temp °C. | $CH_4$ | $C_2H_4$ | $C_2H_6$ | $C_3H_6$ | $C_3H_8$ | $C_4$ | DME |
|---|---|---|---|---|---|---|---|---|
| 10 | 284 | trace |  |  |  |  |  | ~100 |
| 15 |  | Nitrogen diluent passed through p-xylene bubbler | | | | | | |
| 22 | 285 | 0.8 | 11.8 | — | 3.7 | 5.4 | 60.1 | 18.2 |
| 35 | 284 |  |  |  |  |  |  |  |
| 45 |  | Xylene addition stopped | | | | | | |
| 55 | 284 | 1.9 | 13.2 |  | 14.2 | 13.2 | 26.5 | >30 |
| 74 | 274 | 1.6 | 6.8 |  | 14.6 |  | 6.5 | >70 |

(B) % Hydrocarbons

| θ Min | Temp °C. | $C_{1,2}$ | $C_3$ | $C_4$ | TO | XY | AR |
|---|---|---|---|---|---|---|---|
| 10 | 284 |  |  |  |  |  |  |
| 15 | Nitrogen diluent passed through p-xylene bubbler | | | | | | |
| 22 | 285 |  |  |  |  |  |  |
| 35 | 284 | 14.5 | 20.5 | 36.4 | 0 | 6 | 4.6 |
| 45 | Xylene addition stopped | | | | | | |
| 55 | 284 |  |  |  |  |  |  |
| 74 | 274 |  |  |  |  |  |  |

EXAMPLE 35

The catalyst used was that described in Example 33. The feed used was an aqueous methanol mixture (2.75:1, w/w) which was fed across the catalyst at a rate such that the space velocity (W.H.S.V.) of methanol was about 1.3 hr$^{-1}$. In this example pseudo-cumene (1,2,4-trimethylbenzene) was used as aromatic promoter. The results are displayed in Table 16.

TABLE 16

Pseudo-cumene as promoter for methanol conversion over dealuminized mordenite (A) % Light Products

| θ Min | Temp °C. | $CH_4$ | $C_2H_4$ | $C_2H_6$ | $C_3H_6$ | $C_3H_8$ | $C_4$ | DME |
|---|---|---|---|---|---|---|---|---|
| 5 | 284 |  | 0.3 |  |  |  |  | ~100 |
| 12 |  | Nitrogen diluent passed through Pseudo-Cumene in bubbler | | | | | | |
| 22 | 284 | 1.9 | 13.3 |  | 5.2 | 10.9 | 51.0 | ~17 |
| 24 |  | Pseudo-cumene addition stopped | | | | | | |
| 38 | 285 | 2.7 | 16.9 |  |  | 10.4 | 23.7 | 36.8 | ~10 |
| 51 | 284 |  |  |  |  |  |  |  |

(B) % Hydrocarbons

| θ Min | Tem °C. | $C_{1,2}$ | $C_3$ | $C_4$ | TO | XY | AR |
|---|---|---|---|---|---|---|---|
| 5 | 284 |  |  |  |  |  |  |
| 12 |  | Nitrogen diluent passed through Pseudo-cumene in bubbler | | | | | |
| 22 | 284 |  |  |  |  |  |  |
| 24 |  | Pseudo-cumene addition stopped | | | | | |
| 38 | 285 |  |  |  |  |  |  |
| 51 | 284 | 15.0 | 14.8* | 26.7* | 1 | 2 | 6.6 |

*Some DME in $C_3$ analysis ie, below 100% conversion

The results show the beneficial effects of the addition of pseudo-cumene as promoter in facilitating the conversion of methanol (mixed with water) at low temperautes (284° C.). It should be noted that the effect of the promoter persists after addition has stopped leading to the possibility of intermittent addition in order to maintain activity (see Example 31). It should also be noted that the $C_{9+}$ aromatics fraction is low (only about 7%) and the light olefin yield high (ethylene about 15% w/w of hydrocarbons) under these conditions which have been brought about by the promoter. It should also be noted that pseudo-cumene (1,2,4 trimethylbenzene) is a less preferred promoter for the zeolite ZSM-5 because its size does not permit a fast rate of entry into the zeolite pore; this illustrates the point that each zeolite may have different preferred promoters depending upon the size of port of the zeolite.

EXAMPLE 36

This example further illustrates that individual zeolites give differing responses with particular co-catalysts. In this example the same catalyst and conditions as Example 34 were used, the catalyst being regenerated overnight in oxygen at 520° C. before use. The co-catalyst was o-xylene, which was found to be less-preferred for the zeolite ZSM-5 (Example 11). The results are displayed in Table 17.

TABLE 17

Ortho-xylene as promoter in the conversion of methanol over dealuminized mordenite (A) % Light Products

| θ Min | Temp °C. | $CH_4$ | $C_2H_4$ | $C_2H_6$ | $C_3H_6$ | $C_3H_8$ | $C_4$ | DME |
|---|---|---|---|---|---|---|---|---|
| 3 | 285 |  |  |  |  |  |  | 100 |
| 15 |  | Nitrogen diluent passed through o-xylene | | | | | | |

TABLE 17-continued

Ortho-xylene as promoter in the conversion of methanol over dealuminized mordenite

| θ Min | Temp °C. |  |  |  |  |  |  |  |
|---|---|---|---|---|---|---|---|---|
|  |  | bubbler |  |  |  |  |  |  |
| 27 | 285 | 1.9 | 14.3 | — | 6.8 | 11.1 | 53.0 | ~12 |
| 28 |  | o-xylene addition stopped |  |  |  |  |  |  |
| 45 | 284 | 2.5 | 15.2 |  | 11.1 | 19.7 | 31.8 | ~19 |
| 57 | 284 |  |  |  |  |  |  |  |

(B) % Hydrocarbons

| θ Min | Temp °C. | $C_{1,2}$ | $C_3$ | $C_4$ | TO | XY | AR |
|---|---|---|---|---|---|---|---|
| 3 | 285 |  |  |  |  |  |  |
| 15 |  | Nitrogen diluent passed through o-xylene bubbler |  |  |  |  |  |
| 27 | 285 |  |  |  |  |  |  |
| 28 |  | 0-xylene addition stopped |  |  |  |  |  |
| 45 | 284 |  |  |  |  |  |  |
| 57 | 284 | 15.4 | 39.2* | 27.6 | 1 | 0 | 6.0 |

*DME in $C_3$ ie, <100% conversion

This clearly demonstrates the utility of o-xylene addition in bringing about the conversion of methanol over dealuminized mordenite under conditions which favour the production of useful light olefins and low heavy-aromatic formation. It will be realised that because mordenite has a particularly large pore size (12 ring window; faujasite would be expected to be similar) that the range of preferred promoter for mordenite could be large and may include polynuclear aromatic species such as the alkylnaphthalene.

EXAMPLE 37

This example illustrates the use of the invention to produce p-xylene as well as ethylene from methanol using ZSM-5 which apart from activation is unmodified.

The experiment of Example 31 was repeated using the same catalyst and feed (aqueous methanol; 2.75:1) and space velocity (W.H.S.V. 1.33 $hr^{-1}$ on methanol). The results of the experiment are shown in Table 18. The results show that the use of an aromatic promoter is required to produce a useful conversion of oxygenates to hydrocarbon products. After the experiment the liquid products were further analysed and then showed that the xylenes fraction consisted of para-xylene, 83.8%; orthoxylene, 5.0%; and meta-xylene, 11.2%. The product is thus seen to be enriched in para-xylene (expected percentage from thermodynamic consideration is about 25%), and this has been achieved without laborious modifications of the zeolite.

TABLE 18

Formation of p-xylene and ethylene from unmodified ZSM-5

| θ Min | Temp °C. | Volume (%) of effluent gas* |  |  |  |  |  |  |  |  |  |
|---|---|---|---|---|---|---|---|---|---|---|---|
|  |  | $H_2O$ | DME | MeOH | $C_2H_4$ | $C_3H_6$ | $C_3H_8$ | $C_4$ | TO | XY | AR |
| 3.50 | 290 | 88.4 | 4.27 | 4.59 | 0.43 | 0.02 | 0.33 | 0.02 | .001 | .010 | — |
| 3.50 |  | toluene addition of 5% (wt) on methanol |  |  |  |  |  |  |  |  |  |
| 4.45 | 346 | 94.4 | — | — | 1.13 | 0.46 | 0.39 | 0.85 | 0.14 | 0.28 | 0.03 |
| 4.50 |  | toluene addition stopped |  |  |  |  |  |  |  |  |  |
| 5.55 | 320 | 92.1 | 0.79 | 3.50 | 1.95 | 0.13 | 0.95 | 0.40 | 0.01 | 0.17 | — |

*$CH_4$, $C_2H_6$ >0.3%
Temp is maxiumum bed temperature

EXAMPLE 38

This example illustrates the application of the invention to zeolites containing metals such as iron.

An iron containing ZSM-5 was prepared by synthesizing ZSM-5 from a starting gel containing a source of iron oxide. After synthesis the product was calcined and exchanged in order to remove quaternary ammonium salts and sodium and to generate acid sites. The product zeolite contained 1.11%, $Al_2O_3$; 2.11%, $Fe_2O_3$; 0.09%, $Na_2O$.

An experiment was performed in a similar manner to that described for Example 5. Aqueous methanol (2.75:1, wt/wt, water:methanol) was used as feedstock and nitrogen (7 ml $min^{-1}$) used as a diluent carrier-gas. The bubbler containing toluene was maintained at 0° C. The results of the experiment are shown in Table 19.

The results show that the addition of toluene improves the conversion of oxygenates, and the product spectrum is rich in light olefins.

EXAMPLE 39

This example illustrates the use of the invention with a metal-exchanged zeolite, namely Zn-ZSM-5.

The zeolite H-ZSM-5 was transformed to the zinc form of the zeolite by first treating with ammonium hydroxide and then exchanging the resulting $NH_4$-ZSM-5 with a solution containing zinc cations. Before the experiment to be described the Zn-ZSM-5 was brought into activity by calcination to 500° C. and by performing the conversion of methanol to hydrocarbons. As will be appreciated by those skilled in the art, full activity of divalent cation exchanged ZSM-5 zeolites, such as Zn-ZSM-5, is not obtained until the zeolite has been calcined to a high temperature (typically in excess of 400° C.) or used for hydrocarbon conversions at temperatures in excess of about 350° C. This had been done with the catalyst of this example ie it had been brought to full activity and had been regenerated in an atmosphere of oxygen at 500° C.

The experiment of Example 5 was repeated using the Zn-ZSM-5. At a temperature of 313° C. in the absence of toluene promoter, 56% of the light products were oxygenates. After addition of toluene to the nitrogen diluent stream the conversion of oxygenates went to 100%, the yield of ethylene was ca 25% and $C_3$ hydrocarbons, 22%.

TABLE 19

The use of toluene as promoter to aid the conversion of oxygenates by a catalyst containing iron

| θ |  | Temp | Light Products |  |  |  |
|---|---|---|---|---|---|---|
| hr | min | °C. | $C_2H_4$ | $C_3$ | $C_4$ | DME |
| 1 | 00 | 321 | 23 | 23 | 12 | 43 |
| 1 | 30 | 331 | 31 | 32 | 24 | 12 |
| 2 | 30 | 331 | 24 | 27 | 17 | 32 |
| 2 | 35 | Nitrogen diluent passed through toluene bubbler |  |  |  |  |
| 2 | 45 | 331 | 38 | 23 | 36 | 6 |
| 3 | 40 | 325 | 40 | 25 | 36 | nil |
| 3 | 41 | toluene addition stopped |  |  |  |  |
| 3 | 50 | 325 | 29 | 26 | 38 | 11 |

We claim:

1. A process for producing hydrocarbons comprising feeding, under conversion conditions, a charge comprising methanol to a catalyst comprising a crystalline zeolite which has an aluminium content in the range of 0 to 4% w/w, and which is hydrothermally stable in the temperature range of from 250° C. to 500° C. and is capable of converting methanol to hydrocarbons, to form a mixture comprising light olefins, lower alkanes and monocyclic aromatic hydrocarbons and recovering said hydrocarbons; characterized in that the charge consists essentially of water, methanol, in a weight/weight ratio in the range of from 1:5 to 5:1, and a promoter comprising one or more compounds selected from the group consisting of aromatic hydrocarbons wherein the zeolite has a channel size such as to permit sorption and diffusion of the promoter; and wherein the weight/weight ratio of promoter to methanol is in the range of from 0.0001:1 to 1:1, and further characterized in that the charge is substantially free of dimethyl ether.

2. A process according to claim 1 wherein the weight/weight ratio of promoter to methanol is in the range of from 0.01:1 to 0.3:1.

3. A process according to claim 1 wherein the weight/weight ratio of promoter to methanol is in the range of from 0.01:1 to 0.1:1.

4. A process according to claim 1 wherein the catalyst is a faujasite.

5. A process according to claim 1 wherein the catalyst is mordenite.

6. A process according to claim 1 wherein ethylene and propylene constitute a major proportion of the reaction product.

7. A process according to claim 1 wherein the aromatic hydrocarbon is benzene.

8. A process according to claim 1 wherein the aromatic hydrocarbon is benzene substituted with one or more $C_1$ to $C_4$ alkyl groups.

9. A process according to claim 1 wherein the catalyst is of the ZSM-5 family.

10. A process according to claim 8 wherein the aromatic hydrocarbon is toluene.

11. A process according to claim 8 wherein the aromatic hydrocarbon is ethyl benzene.

12. A process according to claim 8 wherein the aromatic hydrocarbon is para-xylene.

13. A process according to claim 9 wherein the catalyst is ZSM-5.

14. A process according to claim 9 wherein the catalyst is ZSM-11.

* * * * *

UNITED STATES PATENT AND TRADEMARK OFFICE
CERTIFICATE OF CORRECTION

PATENT NO. : 4,499,314
DATED : February 12, 1985
INVENTOR(S) : Duncan SEDDON, Thomas MOLE, and Judy A. WHITESIDE It is certified that error appears in the above—identified patent and that said Letters Patent is hereby corrected as shown below:

On the title page;

Delete item "[73] Assignee: Imperial Chemical Industries PLC, London, England"

Signed and Sealed this

Sixth Day of August 1985

[SEAL]

Attest:

DONALD J. QUIGG

Attesting Officer

Acting Commissioner of Patents and Trademarks